United States Patent [19]

Ryan et al.

[11] Patent Number: 4,973,578
[45] Date of Patent: Nov. 27, 1990

[54] SYNTHETIC PEPTIDES DERIVED FROM THE ALPHA-SUBUNIT OF HUMAN LYCOPROTEIN HORMONES

[75] Inventors: Robert J. Ryan; Daniel J. McCormick; John C. Morris; M. Cristine Charlesworth, all of Rochester, Minn.

[73] Assignee: Mayo Foundation for Medical Education and Research, Rochester, Minn.

[21] Appl. No.: 169,375

[22] Filed: Mar. 17, 1988

[51] Int. Cl.$^5$ .................. C07K 7/08; C07K 15/14; A61K 37/38; A61K 37/02
[52] U.S. Cl. .................................. 514/12; 514/13; 514/14; 514/8; 530/325; 530/326; 530/324; 530/395; 530/397; 530/850; 530/854
[58] Field of Search ............... 530/395, 397, 854, 324, 530/326, 850, 325; 514/13, 14, 12, 23, 8

[56] References Cited

U.S. PATENT DOCUMENTS 3,941,763  3/1976  Sarantakis ........................ 530/313
4,609,622  9/1986  Kohn .............................. 435/240.3

OTHER PUBLICATIONS

P. Licht et al., *Recent Prog. Horm. Res.*, 33:169–248 (1977).
J. L. Vaitukaitis et al., *Recent Prog. Horm. Res.*, 32:289–331 (1976).
D. N. Ward et al., *Recent Prog. Horm. Res.*, 29:533–561 (1973).
H. Papkoff et al., *Recent Prog. Horm. Res.*, 29:563–590 (1973).
R. E. Canfield et al., *Recent Prog. Horm. Res.*, 27:121–164 (1971).
J. G. Pierce et al., *Recent Prog. Horm. Res.*, 27:165–212 (1971).
R. J. Ryan et al., *Recent Prog. Horm. Res.*, 26:105–137 (1970).
Ascoli and Segaloff, *J. Biol. Chem.*, 261:3807–3815 (1986).
Grasso and Crisp, *Endocrinology*, 116:319–327 (1985).

Ji and Ji, *Proc. Natl. Acad. Sci. USA*, 78:5465–5469 (1981).
Moudgal and Li, *Proc. Natl. Acad. Sci. USA*, 79:2500–2503 (1982).
Pierce and Parsons, *Ann. Rev. Biochem.*, 50:465–495 (1981).
Armstrong et al., *Biochemical Actions of Hormones*, 13:91–128 (1986).
Davies and Platzer, *Clinical Endocrinology*, 19:427–435 (1983).
Fahraeus-van Ree and Farid, *Clinical Research*, 31, No. 3 (1983).
Smith and Buckland, *Receptors, Antibodies and Disease: Ciba Foundation Symposium* 90, pp. 114–132 (Pitman, London, Pub., 1982).
Volpe, "Pathogenesis of Autoimmune Thyroid Disease", *The Thyroid: A Fundamental and Clinical Text*, pp. 747–767 (5th ed., 1986).
Hagenmaier and Frank, *Hoppe-Seyler's Z. Physiol. Chem.*, 353:1973–1976 (1972).
Kaiser et al., *Anal. Biochem.*, 34:595–598 (1970).
Stewart and Young, *Laboratory Techniques in Solid Phase Peptide Synthesis*, pp. 53–124 (Pierce Chem. Co., Pub. 2d ed. 1984).
Ambesi-Impiombato et al., *Proc. Natl. Acad. Sci. USA*, 77:3455–3459 (1980).

(List continued on next page.)

*Primary Examiner*—F. T. Moezie
*Attorney, Agent, or Firm*—Merchant, Gould, Smith, Edell, Welter & Schmidt, P.A.

[57] ABSTRACT

Synthetic peptides corresponding to α-subunit of human glycoprotein hormone amino acid regions α31–45, α21–35, α26–46 and α81–92; were found to inhibit binding of $125_{I\text{-}bTSH}$ to human thyroid. Peptides corresponding to regions α26–46 and α31–45 were also found to potently inhibit the stimulation of adenylate cyclase activity by bTSH in a TSH bioassay using FRTL-5 cells and block the action of thyroid stimulating immunoglobulin.

7 Claims, 8 Drawing Sheets

OTHER PUBLICATIONS

Lee and Ryan, *Biochemistry*, 12:4609–4615 (1973).
Takahashi et al., *J. Clinical Endocrinol. Metab.*, 47:870–876 (1978).
Bidey et al., *J. Endocr.*, 101:269–276 (1984).
Kasagi et al., *Acta Endocrinol.*, 115:30–36 (1987).
Tramontano and Ingbar, *Endocrinology*, 118:1945–1951 (1986).
Steiner et al., *J. Biol. Chem.*, 247:1106–1113 (1972).
Wray and Glinos, *Am. J. Physiol.*, 234(5):C131–C138 (1978).
Klee and Hay, *J. Clin. Endocrinol. Metab.*, 64:461–471 (1987).
Furmaniak et al., *Acta Endocrinol.*, Suppl. 281:157–165 (1987).
Furmaniak et al., *Program of the 62nd Meeting of the American Thyroid Association*, p. T-62 (1987).
Bishop and Ryan, *Biochemistry*, 12:3076–3084 (1973).
Canfield et al., *Studies of Human Chorionic Gonadotropin*, pp. 121–164 (1971).
Charlesworth, McCormick, Madden, and Ryan, *J. Biol. Chem.*, 262:13409–13416 (Oct. 5, 1987).
Keutmann et al., *Hoppe-Seyler's Z. Physiol. Chem.*, 355:935–938 (1974).
Licht et al., *Evolution of Gonadotropin Structure and Function*, pp. 169–248 (1977).
Papkoff et al., *Studies on the Structure and Function of Interstitial Cell-Stimulating Hormone*, pp. 563–590 (1972).
Pierce et al., *Studies on the Structure of Thyrotropin: Its Relationship to Luteinizing Hormone*, pp. 165–212 (1971).
Ryan et al., *Some Physical and Hydrodynamic Properties of Human FSH and LH*, pp. 105–137 (1969).
Ryan et al., *Recent Prog. Horm. Res.*, 43:383–429 (Jun., 1987).
Smith et al., *Endocrine Reviews*, 9:106–121 (Feb., 1988).
Vaitukaitis et al., *Gonadotropins and Their Subunits: Basic and Clinical Studies*, pp. 289–331 (1975).
Ward et al., *Chemical Studies of Luteinizing Hormone from Human and Ovine Pituitaries*, pp. 533–561 (1972).

SYNTHETIC PEPTIDES DERIVED FROM THE ALPHA-SUBUNIT OF HUMAN LYCOPROTEIN HORMONES

This invention was made with Government support under grant number HD 9140 by the National Institute of Health and funds from the Mayo Foundation. The Government has certain rights in the invention.

BACKGROUND OF THE INVENTION

The gonadotropins, luteinizing hormone (LH) and follicle-stimulating hormone (FSH) of pituitary origin, and chorionic gonadotropin (hCG, eCG) of placental origin, along with thyroid-stimulating hormone (TSH) constitute a family of glycoprotein hormones. Their isolation, characterization, and biological functions have been the subject of numerous reports. [Licht et al., *Recent Prog. Horm. Res.*, 33:169 (1977); Vaitukaitis et al., *Recent Prog. Horm. Res.*, 32:289 (1976); Ward et al., *Recent Prog. Horm. Res.*, 29:533 (1973); Papkoff et al., *Recent Prog. Horm. Res.*, 29:563 (1973); Canfield et al., *Recent Prog. Horm. Res.*, 27:121 (1971); Pierce et al., *Recent Prog. Horm. Res.*, 27:165 (1971); Ryan et al., *Recent Prog. Horm. Res.*, 26:105 (1970)].

Human glycoprotein hormones (TSH, LH, FSH and hCG) are heterodimers consisting of a hormone specific Beta-subunit and a common α-subunit, [Pierce, and Parsons, *Ann. Rev. Biochem,* 50, 465, (1981)]. The intact dimer may be necessary for full biological activity; however, data on the gonadotropic hormones LH and hCG indicate that both the Alpha and Beta subunits interact with the receptor [Ji and Ji, *Proc. Natl. Acad. Sci. U.S.A.*, 78:5465–5469 (1981); Ascoli and Segaloff, *J. Biol. Chem.*, 261:3807–3815 (1986); Moudgal and Li, *Proc. Natl. Acad. Sci. U.S.A.*, 79:2500–2503 (1982); Grasso and Crisp, *Endocrinology,* 116:319–327 (1985); and Armstrong et al., *Biochemical Actions of Hormones,* 13:91–128 (1986).

To understand the extent to which the particular subunits contribute to the activity of the intact dimer, a need exists to isolate and characterize the subset of peptides within the subunits, including α-subunit peptides, which are responsible for the range of biological activities associated with human glycoprotein hormones. Lower molecular weight oligopeptides corresponding to a subunit sequence would be expected to be more readily obtainable, less expensive and exhibit a narrower profile of biological activity than glycoprotein hormones themselves, thus increasing their potential usefulness as therapeutic or diagnostic agents.

One particular human glycoprotein hormone of interest is TSH. The structure and function of TSH are of interest in part due to the hormone's role in thyroid disorders. One such disorder is Graves' disease, an autoimmune disease which occurs most often in women and involves over production of thyroxin by the thyroid.

Graves' disease is characterized by the presence of immunoglobulins (autoantibodies) that inhibit the binding of TSH to its receptor (thyrotropin binding inhibiting immunoglobulin, TBII) and increase adenylate cyclase activity (thyroid stimulating immunoglobulin, TSI or TRAb) in thyroid follicular cells [Volpe, *The Thyroid: A Fundamental and Clinical Text,* p. 747 (5th ed. 1986)]. The interaction between TSI and TSH receptor has been carefully studied [Smith and Buckland, *Receptors, Antibodies, and Disease CIBA Foundation Symposium,* p. 114 (1982); Fahraeus-Van Ree and Farid, *Clin. Res.,* 31:679A (1983); Davies and Platzer, *Clin. Endocrinol.,* 19:427 (1983)] and current evidence, suggests that the thyrotropin receptor itself is the antigen [Smith and Buckland, supra]. However, the specific binding site remains unknown.

Individuals affected with Graves' disease exhibit exophthalomos, enlarged pulsating thyroid gland, marked acceleration of the heart rate, a tendency to profuse sweats, nervous symptoms, psychic disturbances, emaciation, increased metabolic rate, and pretibial myxedma. Recognized treatment of Graves' disease involves inactivation of the thyroid gland with radioactive iodine, surgical removal of the gland or treatment with certain antithyroid drugs such as propylthiouracil. While present treatments can alleviate the metabolic disorders, they do not prevent continued exophthalomos and pretribial myxedema. The inability to arrest these manifestations may, in part, be due to the failure of current treatments to inhibit binding of long-acting thyroid stimulator (TSI) to cells in the orbit of the eye and skin.

Therefore, there is a need to study and obtain synthetic α-subunit peptides of human glycoprotein hormones or analogues thereof which can inhibit TSH binding to human thyroid membrane; inhibit TSH mediated cAMP generation; and also block the action of TSI and block the binding of LH and hCG to their receptors.

SUMMARY OF THE INVENTION

The present invention provides polypeptides which represent fragments of the α-subunit of human glycoprotein hormones. The peptides can be prepared by modified conventional solid phase peptide synthesis. The polypeptide fragments of the present invention correspond substantially to human glycoprotein hormone α-subunit amino acid residues α21-35, α26-46 and α31-45 and include functional analogues of these α-subunit poly peptides. The preferred polypeptide is:

Leu-Gln-Cys-Met-Gly-Cys-Cys-Phe-Ser-Arg-Ala-Tyr-Pro-Thr-Pro-Leu-Arg-Ser-Lys-Lys-Thr(NH$_2$)

corresponding to isolated α-subunit residues 26-46 of glycoprotein hormones TSH, LH, FSH and hCG.

The polypeptides of the present invention were assayed for bioactivity and found to (a) inhibit binding of TSH to human thyroid membrane and FRTL-5 rat thyroid cells; and (b) inhibit TSH mediated cAMP generation. In a preferred embodiment the polypeptide of the present invention inhibited TSH mediated cAMP generation by between about 90 and 100%. The preferred polypeptide α26-46 showed surprisingly potent inhibition of TSH; however, peptides corresponding to α-subunit regions 31-45 and 21-35 also inhibit binding of TSH.

Polypeptides corresponding to α-subunit regions α31-45 and α26-46 strongly inhibited the stimulation of adenylate cyclase activity by bTSH in a TSH bioassay using FRTL-5 cells and also inhibited the stimulatory activity of thyroid stimulating immunoglobulin (TSI) from patients with Graves' disease. The α26-46 peptide demonstrated an inhibitory effect on the binding of thyroid stimulating immunoglobulin to FRTL-5 cells in 10 of 10 patients with Graves' disease.

In view of the common α-subunit of LH, hCG and TSH, peptides or analogues thereof in accordance with the present invention may be useful to block LH and hCG binding to their receptors. Thus, use of peptides or analogues according to the present invention provide for potential contraceptives and/or preparation of contraceptive vaccine.

The polypeptides of the present invention also possess characteristics which can be applied for immunodiagnostic and immunotherapy purposes. Antibodies raised in response to polypeptides of the present invention can be used as an immunodiagnostic to measure TSI in a patient sample. Also, antibodies raised in response to polypeptides of the present invention can be used therapeutically to neutralize TSI.

DETAILED DESCRIPTION OF THE INVENTION

Figure 1:
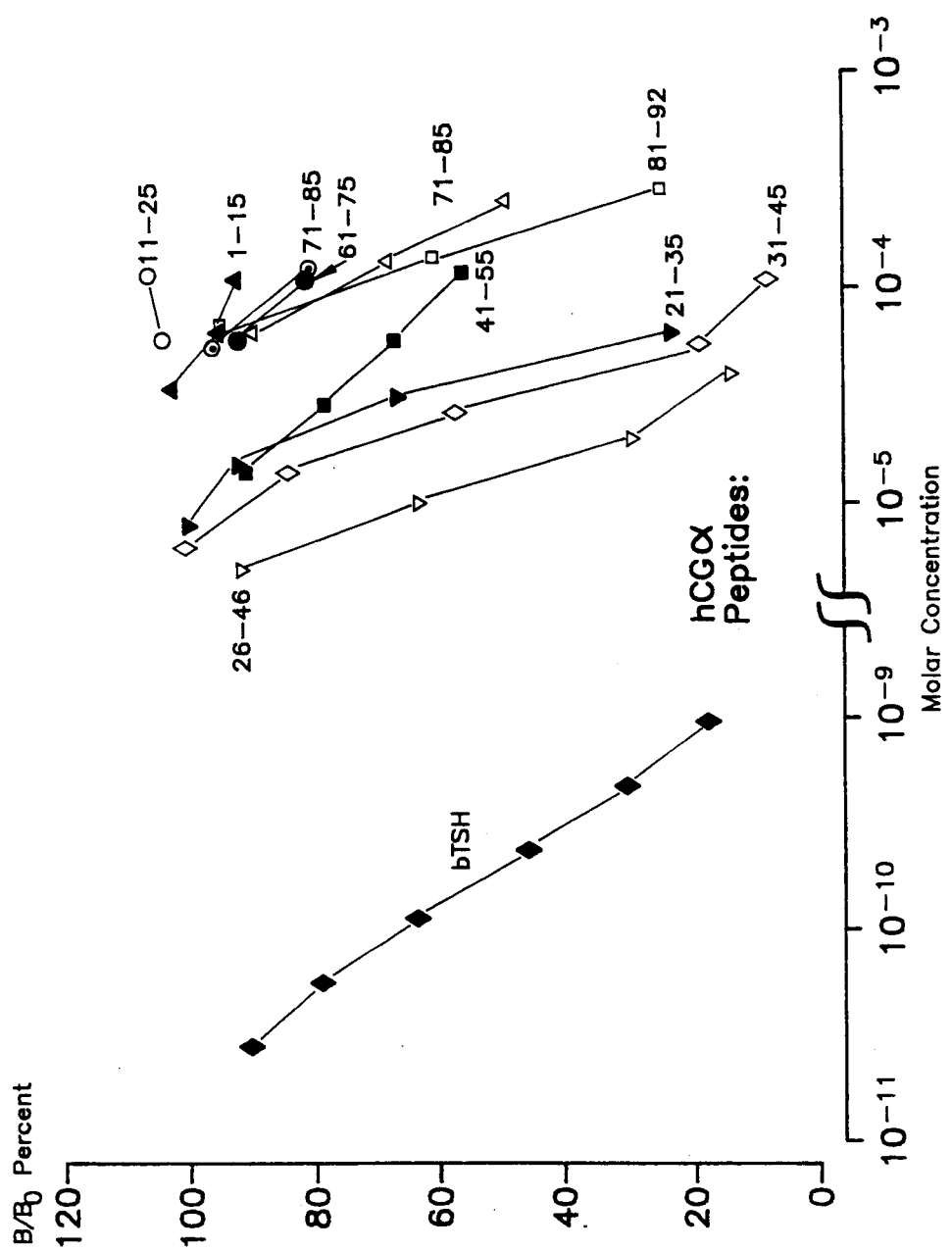
FIG. 1 is a graph depicting inhibition of $^{125}$I-bTSH binding to human thyroid membrane preparations by synthetic α-subunit peptides.

We prepared ten synthetic α-subunit peptides to study the structure-function relationships of the peptide sequence of the TSH hormone. The receptor binding and biologic activity of these synthetic α-subunit peptides in a human thyroid membrane system and the functional rat thyroid follicular cell line FRTL-5 were evaluated. Specifically, the ability of the synthetic peptide fragments of the α-subunit of human glycoprotein hormones to interact with the TSH receptor on both human thyroid membranes and intact FRTL-5 cells was studied. The ability of the synthetic peptide fragments to inhibit TSH mediated cAMP generation was also studied. Selected fragments were evaluated for blocking action of long-acting thyroid stimulator (known as LATS or TSI, thyroid stimulating immunoglobulin).

Synthesis of Polypeptides

Nine synthetic overlapping peptides of human glycoprotein hormone α-subunit and a 21 amino acid residue synthetic peptide corresponding to the sequence α26-46, represented in Table 1, were synthesized by a modified solid-phase method on an automated 430A peptide synthesizer (Applied Biosystems, Inc., CA.)

Table 1 shows the overlapping strategy of the peptide sequences. Each peptide consists of 15 amino acids and overlaps with its neighboring two peptides by 5 amino acids except for the longer α26-46 peptide. Thus, the complete 92 amino acid sequence of the α-subunit is represented by the 10 peptides.

TABLE 1

| Peptide | Sequence |
| --- | --- |
| α 1-15: | Ala—Pro—Asp—Val—Gln—Asp—Cys—Pro—Glu—Cys—Thr—Leu—Gln—Glu—Asn |
| α11-25: | Thr—Leu—Gln—Glu—Asn—Pro—Phe—Phe—Ser—Gln—Pro—Gly—Ala—Pro—Ile |
| α21-35: | Pro—Gly—Ala—Pro—Ile—Leu—Gln—Cys—Met—Gly—Cys—Cys—Phe—Ser—Arg |
| α31-45: | Cys—Cys—Phe—Ser—Arg—Ala—Tyr—Pro—Thr—Pro—Leu—Arg—Ser—Lys—Lys |
| α41-55: | Leu—Arg—Ser—Lys—Lys—Thr—Met—Leu—Val—Gln—Lys—Asn—Val—Thr—Ser |
| α51-65: | Lys—Asn—Val—Thr—Ser—Glu—Ser—Thr—Cys—Cys—Val—Ala—Lys—Ser—Tyr |
| α61-75: | Val—Ala—Lys—Ser—Tyr—Asn—Arg—Val—Thr—Val—Met—Gly—Gly—Phe—Lys |
| α71-85: | Met—Gly—Gly—Phe—Lys—Val—Glu—Asn—His—Thr—Ala—Cys—His—Cys—Ser |
| α81-92: | Ala—Cys—His—Cys—Ser—Thr—Cys—Tyr—Tyr—His—Lys—Ser(OH) |
| α26-46: | Leu—Gln—Cys—Met—Gly—Cys—Cys—Phe—Ser—Arg—Ala—Tyr—Pro—Thr—Pro—Leu—Arg—Ser—Lys—Lys—Thr—(NH$_2$) |

Primary structures of the synthetic overlapping glycoprotein α-subunit peptides The numbers refer to the position of residues in the α-subunit. The underlined residues represent the regions on each peptide that overlap with its two adjacent neighbors. Also included is the sequence of peptide α26-46.

All of the synthetic peptides (0.5 mmol/each), except sequence 81-92(OH) were synthesized on p-methylbenzhydrylamine resin (ABI, 0.48 mmol of amine/g of copolystyrene resin) with Boc-L-amino acid derivatives according to the coupling schedule listed in Table 2. Peptide α81-92 was synthesized on 4-oxymethylphenylacetamidomethyl resin (0.72 mmol/g) yielding a free carboxyl group on the COOH-terminal serine residue. Each amino acid was added to the peptide chain by a preformed symmetric anhydride method described in Hagenmaier and Frank, *Hoppe Seyler's J. Physiol. Chem.*, 353, 1973–1976 (1972) the disclosure of which is incorporated herein. The amino acids Boc-L-glutamine, Boc-L-asparagine, and Boc-L-arginine (tosyl) were coupled as their 1-hydroxybenzotriazole active esters. Completion of coupling after addition of each amino acid was monitored by the ninhydrin reaction as described in Kaiser et al., *Anal. Biochem.*, 34: 595-598 (1970) the disclosure of which is incorporated herein.

Synthesis of each peptide was performed under the conditions which achieved a greater than 99.6% coupling efficiency in the monitoring of each amino acid. The side chain protecting groups of each Boc amino acid employed in synthesis were: e-2-chlorobenzyloxycarbonyl for lysine; O-2-bromobenzyloxycarbonyl for tyrosine; β- and γ-benzyl esters for aspartic and glutamic acids, respectively; $N^{im}$-toluenesulfonyl for histidine; O-benzyl for serine and threonine; S-4 methylbenzyl for cysteine; and $N^g$-toluenesulfonyl for arginine.

The completed peptides (0.5 mmol) were removed from the resin support by acidolysis for 60 min at 0° C. with 10 ml of liquid hydrogen flouride containing 1.0 ml of thioanisole and 1.0 ml of dimethylsulfide and were extracted into 25 ml of trifluoroacetic acid. Synthetic peptides containing the residues Met or Cys were extracted in trifluoroacetic acid containing 1.0% dithiothreitol (w/v). The extracted peptides were then precipitated into cold diethyl ether (4° C.), washed three times with cold ether, and then redissolved in 1M acetic acid before lyophilization. Each lyophilized crude peptide (200–500 mg) was initially purified on a column (1.6×95 cm) of Sephadex G-50 (Pharmacia Biotechnology, Inc., superfine) using a 0.1M pyridine/acetic acid buffer, pH 4.3, containing 0.5% acetonitrile (v/v). Peptides 26-46, 31-45 and 81-92 were further purified by ion-exchange chromatography on a column (1.6×50 cm) of DEAE-Sephacel (Pharmacia Biotechnology, Inc.) in 0.05M pyridine/acetate buffer, pH 4.5.

After gel filtration, 200 ug of each peptide was subjected to high voltage paper electrophoresis (Savant FP30A, 3000 V, 55 min) in 0.05M pyridine/acetate buffer, pH 6 or 3.5, to test for homogeneity. Additionally, each synthetic peptide (2–6 nmol) was microsequenced on a 470A gas-phase protein sequenator (Applied Biosystems), employing computer programs (version 3-03 CPTH) provided by the manufacturer. Resultant phenylthiohydantoins were identified by reversed-phase HPLC using an on-line 120A PTH analyzer (Applied Biosystems).

TABLE 2

Coupling schedule for solid-phase peptide synthesis

| Step | Operation and Reagents[a] | Mixing Time min. |
|---|---|---|
| 1 | DCM wash of Boc-aa resin (0.5 mmol), repeat 3 times | 1.0 |
| 2 | Deprotection, 65% TFA containing 0.5% anisole (v/v), 0.2% indole (wt/v) | 2.0 |
| 3 | Deprotection, 65% TFA containing 0.5% anisole (v/v), 0.2% indole (wt/v) | 20.0 |
| 4 | DCM wash, repeat 3 times | 1.0 |
| 5 | Neutralization, 25% DIEA in DCM (v/v) | 2.0 |
| 6 | DCM wash, repeat 2 times | 0.5 |
| 7 | Neutralization, 25% DIEA in DCM (v/v) | 5.0 |
| 8 | DCM wash, repeat 3 times | 1.0 |
| 9 | DMF wash, repeat 3 times | 1.0 |
| 10 | Coupling, Boc-aa anhydride (1.0 mmol) in DMF (prepared from Boc-aa (2 mmol) + DCC (1.0 mmol); filtered from DCHU and concentrated in DMF by evaporation with $N_2$) | 120–480 |
| 11 | DMF wash, repeat 3 times | 2.0 |
| 12 | DMF/DCM wash, (50%, v/v), repeat 2 times | 1.0 |
| 13 | DCM wash, repeat 3 times | 2.0 |
| 14 | Coupling check; repeat from Step 5 for recycle | |
| 15 | Repeat Step 2 for coupling of each Boc-aa | |

[a]The abbreviations used are: Boc-aa, t-butyloxycarbonyl-L-amino acid; DCM, dichloromethane; TFA, trifluoroacetic acid; DIEA, diisopropylethylamine; DMF, Dimethylformamide; DCC, dicyclohexylcarbodiimide (0.5 M DCM (w/w)); DCHU; dicyclohexylurea.

All organic solvents employed for synthesis were anhydrous and of HPLC grade purity. Reagents DCM, DIEA, and DPIF were of HPLC grade or purified by fractional distillation as described by Stewart and Young, *Solid Phase Peptide Synthesis*, Pierce Chemical Company, Pub. Rockford, Ill. (2ed 1984) the disclosure of which is incorporated by reference herein.

Membrane Preparation.

Thyroid tissue obtained at surgery from patients with Graves' disease was prepared as described by Takahashi et al., *J. Clin. Endocrinol. Metab.* 47:870 (1978), the disclosure of which is incorporated herein. Briefly, the tissue was dissected free of fibrous material, minced with scissors, and homogenized with Polytron homogenizer. The 2000×g fraction was collected by centrifugation, washed and resuspended in 40 mM Tris, 0.1% Bovine Serum Albumin (BSA) pH 7.4 at a concentration of 100 mg equivalents of wet tissue per milliliter. The preparation was stored at −70° C. until used for assay.

Cell Cultures

FRTL-5 cells were maintained in Ham's F-12 medium supplemented with 5% calf serum and a 6 hormone preparation including 10 mU/ml bTSH as described by Ambesi-Impiombato et al., *Proc. Natl. Acad. Sci. U.S.A.*, 77:3455 (1980), the disclosure of which is incorporated herein. For all assays herein described, the cells were plated in 24 well plates and grown for 3 days at 37° C. then maintained for 5–7 days in medium supplemented with 10 ug insulin alone prior to assay.

TSH Radioreceptor Assays.

Highly purified bovine TSH (30 IU/mg, supplied by Dr. J. G. Pierce, UCLA) was radio-iodinated ($Na^{125}I$, Amersham, Chicago) by a gentle lactoperoxidase procedure described by Takahashi et al., supra, then purified by Sephadex G-100 chromatography. The product had a specific activity of 50–75 uCi/ug and retained greater than 90% of original biopotency as determined by a self-displacement radioreceptor and radioimmunoassay (RIA) performed in accordance with procedures by Lee and Ryan, *Biochem.*, 12:4609 (1973) the disclosure of which is incorporated by reference herein.

The membrane assay incubation mixture consisted of 100 mg equivalents of the 2000×g membrane fraction, 0.125 ng $^{125}I$ bTSH (approximately 20,000 cpm, 5×10$^{-12}$M), 100 ul of 1% Triton X-100 and noted amounts of test materials in a final volume of 0.5 ml of 40 mM Tris-HCl pH 7.4 plus 0.1% BSA. Nonspecific binding was determined by addition of excess unlabeled bTSH (200 mU/ml, Sigma, St. Louis). After 2 hrs incubation at 25° C., 200 ul of 5 mg/ml bovine gamma globulin and 1 ml 30% polyethylene glycol 6000 (Baker, Phillipsburg, N.J.) in 1M NaCl was added to each tube and the tubes centrifuged at 4000 rpm for 25 minutes.

The supernatants were aspirated and pellets counted in a gamma counter. Specific binding averaged 25% of total counts.

Binding studies were also performed with intact FRTL-5 cells as the receptor source, utilizing the procedure described by Tranontano and Ingbar, *Endocrinol.*, 118:1945 (1986) the disclosure of which is incorporated herein. TSH deprived cells were washed with binding buffer (NaCl-free Hank's buffered salt solution (HBSS), 200 mM sucrose, 0.5% BSA, pH 7.0 (Tranontano and Ingbar, supra), then incubated for 6 hours at 25° C. with 0.125 ng $^{125}$I-bTSH and varying concentrations of synthetic α-subunit peptides in 300 ul buffer. The cells were then washed three times with buffer, solubilized with 1 ml 1N NaOH, and counted in a gamma counter. Nonspecific binding was measured in the presence of excess unlabeled bTSH as above. Total specific binding averaged 12–15% of added counts.

TSH Bioassay

The bioassay was a modification of those previously described by Bidey et al, *J. Endocrinol.*, 101:269 (1984); and Kasagi et al., *ACTA Endocrinol.*, 115:30 (1987). To duplicate culture wells were added varying concentrations of test materials (see below) in a final volume of 300 ul of NaCl free HBSS with 0.5 mM iso-butyl-methyl-xanthine (IBMX, Sigma, St. Louis). In stimulation assays, only synthetic α-subunit peptides were added to the incubation medium. For inhibition assays, the noted concentrations of synthetic α-subunit peptides were added immediately prior to the addition of 200 mU/L bTSH. The plates were incubated at 37° C. in 5% $CO_2$ for 2 hrs then 100 ul of incubation medium was removed and diluted in 900 ul of 0.05M sodium acetate pH 6.2 and assayed for cAMP content by RIA in accordance with procedures described by Wray and Glinos, *Am. J. Physiol.*, 234 (Cell Phisiol. 3):C131(1978)); and Steiner et al., *J. Biol. Chem.*, 247:1106 (1972). The sensitivity of the bioassay was such that 10 mU/L bTSH resulted in a 2.5±0.2 (m±sd) fold increase in cAMP levels over basal. Basal cAMP levels were determined in the presence of HBSS and IBMX alone. In inhibition assays percent inhibition was calculated as follows:

$$\% \text{ Inhibition} = 100 \times \left[ 1 - \frac{(p\text{moles } cAMP \text{ sample} - p\text{moles basal})}{(p\text{moles } cAMP \text{ TSH} - p\text{moles basal})} \right]$$

Inhibition of $^{125}$I-bTSH Binding To Human Thyroid Membrane Preparations By Synthetic α-Subunit Peptides Adding synthetic peptides α31-45, α21-35, α26-46, α41-55, and α81-92 to the TSH radioreceptor assay resulted in dose dependent inhibition of binding of $^{125}$I-bTSH to human thyroid membranes. The displacement curves for these findings comparing intact bTSH to the synthetic α-subunit peptides are shown in FIG. 1. FIG. 1 reports $5 \times 10^{-12}$M labeled bTSH incubated with 10 mg equivalents (wet weight) of 2000×g fraction of thyroid membranes with varying concentrations of unlabeled TSH or synthetic α-subunit peptides. Nonspecific binding was determined in the presence of excess unlabeled TSH.

As shown in FIG. 1, Peptides α26-46, α31-45, and α21-35 demonstrated the highest potency and were able to displace the label by more than 80% at concentrations greater than $1 \times 10^{-5}$m. Peptides α41-55 and α81-92 also possessed binding activity, but were considerably less potent than α26-46, α31-45 and α21-35. Peptides α1-15 and α11-25 showed no activity at the highest concentration tested and, thus, serve as negative controls for the assay. Peptides α51-65, α61-75, and α71-85 possessed only shallow activity at very high concentrations.

Table 3 shows the dose of peptide required for 50% inhibition of $^{125}$I-bTSH binding ($ED_{50}$).

TABLE 3

Inhibition of $I^{125}$ bTSH Binding to Human Thyroid Membrane Homogenates by Synthetic Glycoprotein Hormone α-Subunit Peptides.

| peptide | n | bTSH $ED_{50}$* $M \times 10^{-5} \pm$ S. E. |
|---|---|---|
| α 1-15 | 3 | >70 |
| α11-25 | 3 | no activity |
| α21-35 | 3 | 3.99 ± 0.04 |
| α31-45 | 5 | 3.12 ± 0.38 |
| α41-55 | 4 | 17.1 ± 2.83 |
| α51-65 | 3 | 23.7 ± 0.95 |
| α61-75 | 4 | >70 |
| α71-85 | 4 | >70 |
| α81-92 | 2 | 17.5 ± 0.38 |
| α26-46 | 2 | 1.08 ± 0.03 |

*The effective dose necessary to inhibit binding of the respective label by 50%. The $ED_{50}$ of unlabeled bTSH is 2.07 ± 0.08 × $10^{-10}$ M.

Inhibition of $^{125}$I-bTSH Binding To FRTL-5 Cells By Synthetic α-Subunit Peptides $^{125}$I-bTSH binding studies were also performed utilizing FRTL-5 cells as the receptor source. Values reported in FIG. 2 reflect TSH deprived FRTL-5 cells incubated with labeled bTSH ($5 \times 10^{-12}$M) and various concentrations of unlabeled bTSH or synthetic peptides. Nonspecific binding was determined in the presence of excess unlabeled TSH. After the wells were washed, bound radioactivity was removed from wells by addition of 1N NaOH. Peptide α21-35 could not be tested in the cell binding assay as it precipitated in the assay buffer; however it remained in solution in the soluble membrane assay (FIG. 1).

Figure 2:
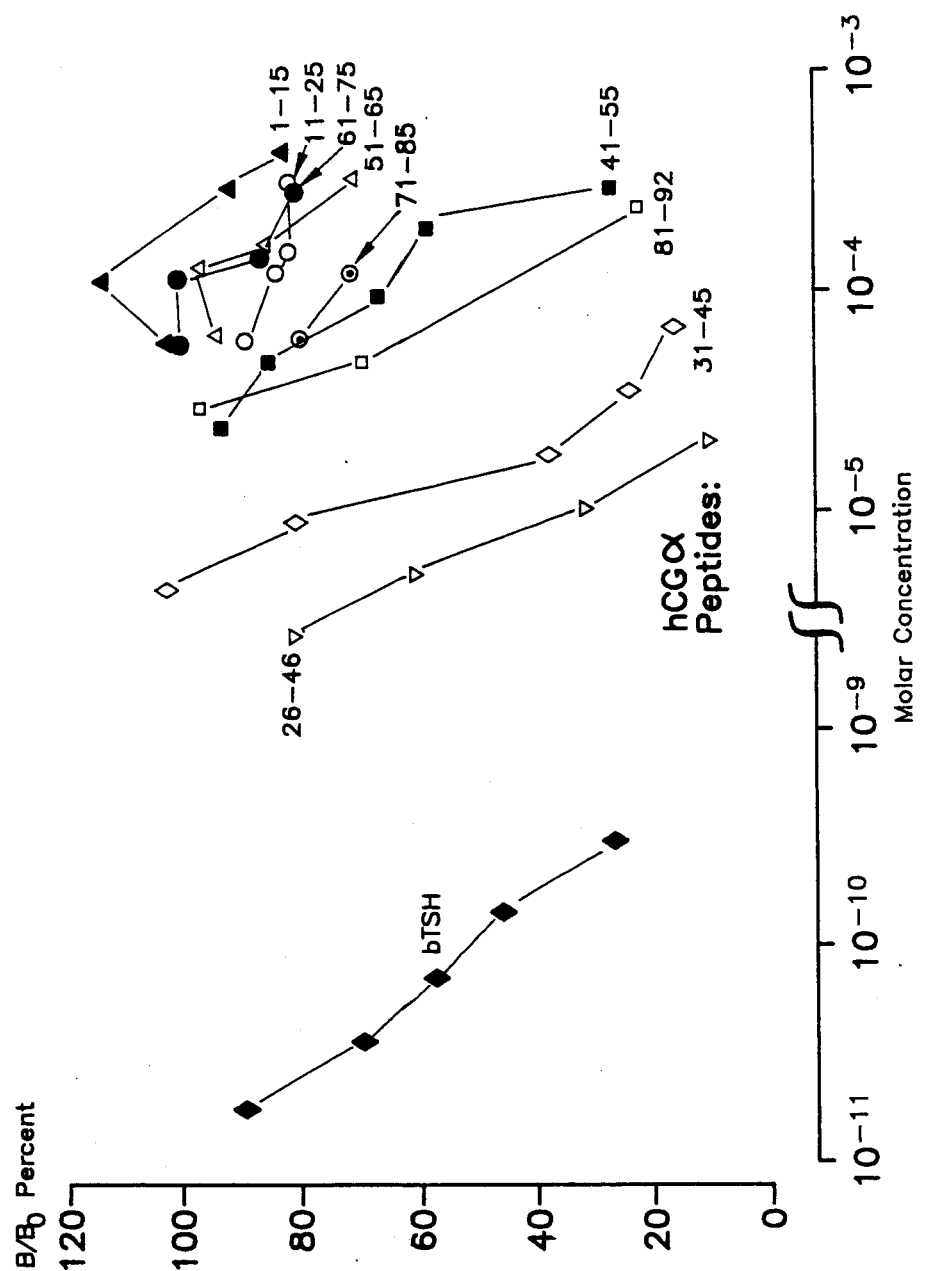
FIG. 2 is a graph depicting inhibition of $^{125}$I-bTSH binding to FRTL-5 cells by synthetic α-subunit peptides.

As shown in FIG. 2 only minor discrepancies between the two assays were observed with respect to activity of the synthetic α-subunit peptides. We believe this indicates that no major interspecies specificity differences exist between the two assays.

cAMP Stimulation Bioassay.

Figure 3:
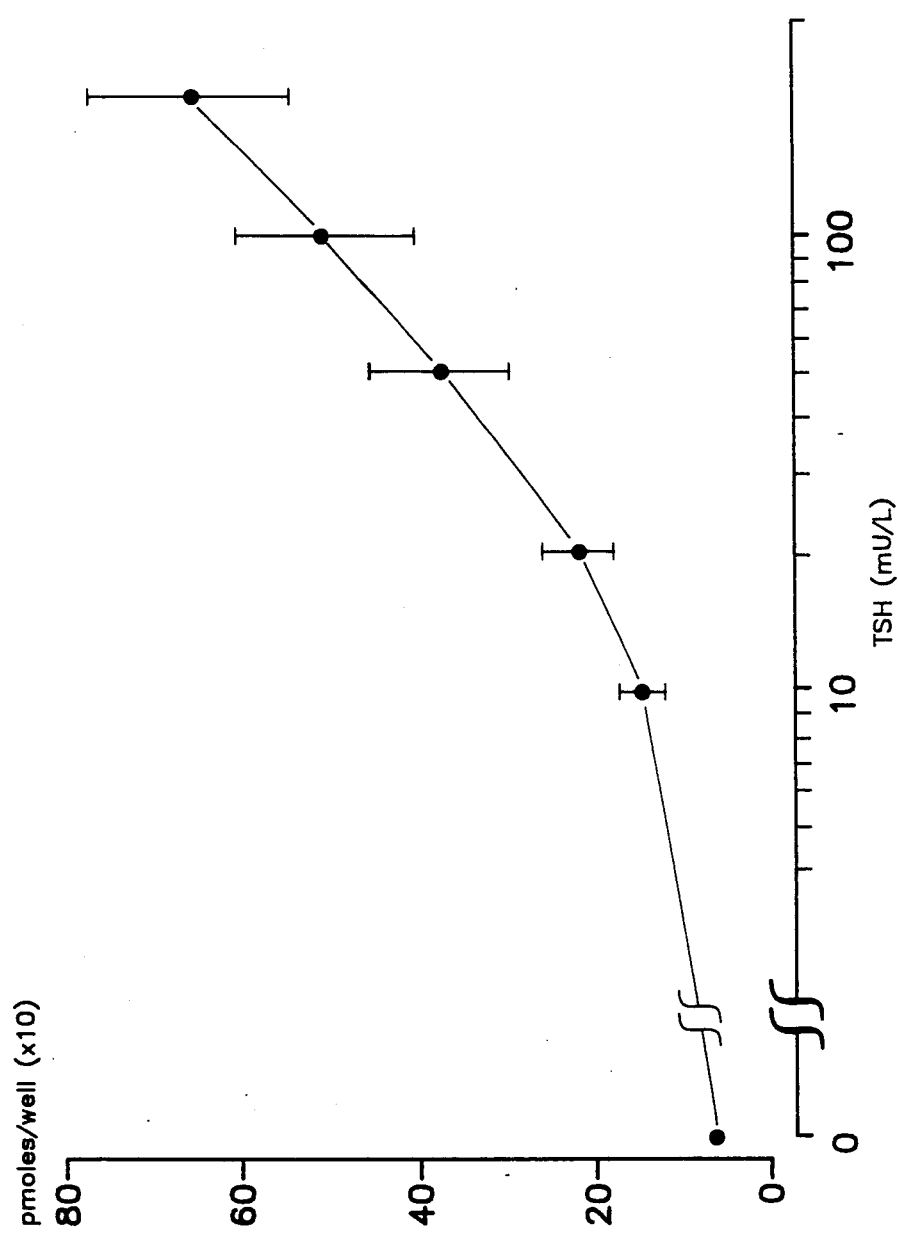
FIG. 3 is a graph depicting TSH bioassay utilizing FRTL-5 cells. The y-axis is cAMP produced and the x-axis is the dose of TSH in milliunits per liter.

The TSH bioassay as performed in FRTL-5 cells demonstrated the ability to detect 10 mU/L bTSH with a 2.5±0.2 fold (m±sd) increase in cAMP levels over basal. The standard curve for TSH is shown in FIG. 3 and reports TSH deprived FRTL-5 cells incubated for 2 hrs. in buffer (NaCl-free HBSS, 200 mM sucrose, 0.5% BSA, 0.5 mM IBMX) with increasing concentrations of bTSH. cAMP released into the incubation media was measured by RIA. Values represent mean±se of duplicates from 4 consecutive assays. Addition of the synthetic α-subunit peptides to the assay did not result in an increase in cAMP levels over basal in at least 2 separate assays, indicating that the peptides, although capable of interacting with the TSH receptor, were incapable of stimulating adenylate cyclase activity.

Inhibition of TSH Mediated cAMP Generation in FRTL-5 Cells.

Figure 4:
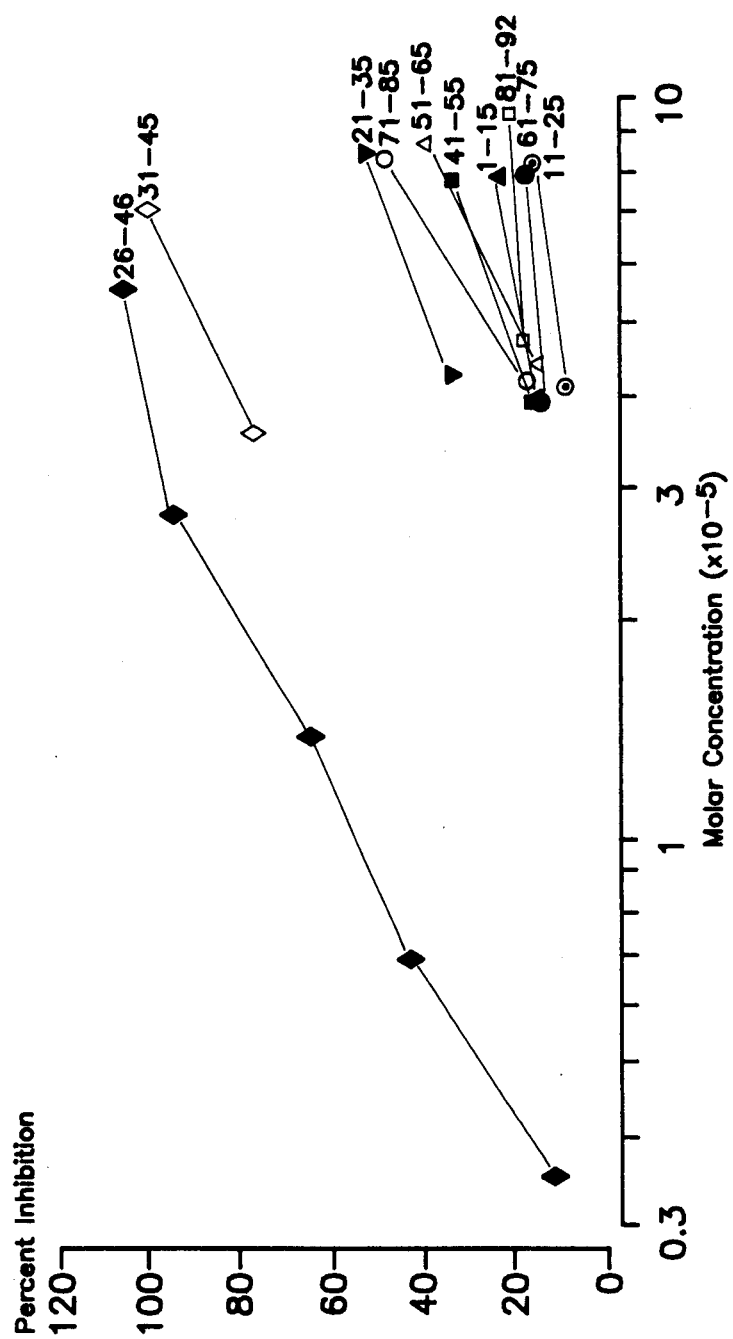
FIG. 4 is a graph depicting inhibition of TSH mediated cAMP generation in FRTL-5 cells by various synthetic peptides.

FIG. 4 reports data obtained for TSH deprived FRTL-5 cells incubated with a fixed amount of bTSH (200 mU/l) by itself or with various concentrations of synthetic peptides. cAMP content of medium was measured after 2 hrs. incubation at 37° C. Percent inhibition of cAMP generation was calculated as noted above.

Addition of 200 mU/L bTSH to the FRTL-5 cell cultures after TSH deprivation resulted in a 10.4±1.6 (m±se) fold rise in cAMP levels over basal at 2 hours. Selected individual synthetic α-subunit peptides, when added to the cultures, resulted in reduction of the cAMP increase seen with the addition of bTSH, while other peptides possessed no significant activity. FIG. 4 and Table 4 show that peptides α31-45 and α21-35 again demonstrated the highest activity with inhibition of 100±0.9% and 52.5×6.6% respectively, at 133.3 ug/ml concentration. Peptides α41-55 and α51-65 as in the binding assay also demonstrated activity in the TSH inhibition assay (34.5±6.5% and 39.9±7.7% respectively at 133.3 ug/ml) but were less potent than the two previously listed peptides. Peptide α71-85 while possessing little ability to displace TSH from its receptor demonstrated some inhibitory activity in the bioassay (17.4±1.3% and 48.7±6.9% at 66.7 and 133.3 ug/ml respectively.) Peptides α1-15, α11-15, and α61-75 did not inhibit TSH activity significantly when tested at the same concentrations as the active peptides and thus serve as negative controls for the assay. Peptide α81-92, although it showed weak inhibition of TSH binding (FIG. 1), did not significantly inhibit TSH stimulation of cAMP production.

The peptide, α26-46, containing portions of the α21-35 sequence and the entire α31-45 sequence was tested in the bioassay. As with the previous peptides α26-46 had no ability to stimulate cAMP production, but was more potent at inhibiting TSH mediated cAMP generation than either α31-45 or α21-35 demonstrating 65.0±2.6%, 95.6±3.1%, and 106±0.8% inhibition at 33.3, 66.6 and 133.3 ug/ml respectively (FIG. 4 and Table 4). Based on the above the region corresponding to amino acids α26-46 possesses the most potent activity in both radioreceptor and bioassays.

TABLE 4

Inhibition of TSH Mediated cAMP Generation in FRTL-5 Cells by Synthetic α-subunit

| ligand | concentration ug/ml | [M] × 10$^{-5}$ | n | percent inhibition mean ± s.e. |
|---|---|---|---|---|
| α26–46 | 33.3 | 1.41 | 3 | 64.97 ± 2.62 |
|  | 66.7 | 2.81 | 5 | 95.62 ± 3.07 |
|  | 133.3 | 5.62 | 2 | 106.70 |
| α31–45 | 66.7 | 3.60 | 3 | 77.50 ± 3.18 |
|  | 133.3 | 7.19 | 3 | 100.63 + 0.90 |
| α21–35 | 66.7 | 4.27 | 4 | 33.88 ± 4.11 |
|  | 133.3 | 8.53 | 5 | 52.50 ± 6.63 |
| α81–92 | 66.7 | 4.76 | 3 | 18.03 ± 3.29 |
|  | 133.3 | 9.51 | 3 | 20.83 ± 8.68 |
| α41–55 | 66.7 | 3.89 | 4 | 16.61 ± 9.33 |
|  | 133.3 | 7.78 | 3 | 34.30 ± 6.45 |
| α51–65 | 66.7 | 4.41 | 3 | 16.23 ± 3.32 |
|  | 133.3 | 8.81 | 3 | 39.90 ± 7.71 |
| α71–85 | 66.7 | 4.17 | 3 | 17.43 ± 1.31 |
|  | 133.3 | 8.33 | 3 | 48.67 ± 6.87 |
| α61–75 | 66.7 | 3.93 | 3 | 15.04 ± 4.09 |
|  | 133.3 | 7.86 | 3 | 17.79 ± 5.60 |
| α 1–15 | 66.7 | 3.92 | 2 | 15.55 |
|  | 133.3 | 7.84 | 2 | 24.00 |
| α11–25 | 66.7 | 4.10 | 2 | 9.25 |
|  | 133.3 | 8.20 | 2 | 16.30 |

Inhibition Of Thyroid Stimulating Immunoglobulin (TSI) By Synthetic Peptides Of Human Glycoprotein Hormone α-Subunit

Figure 5:
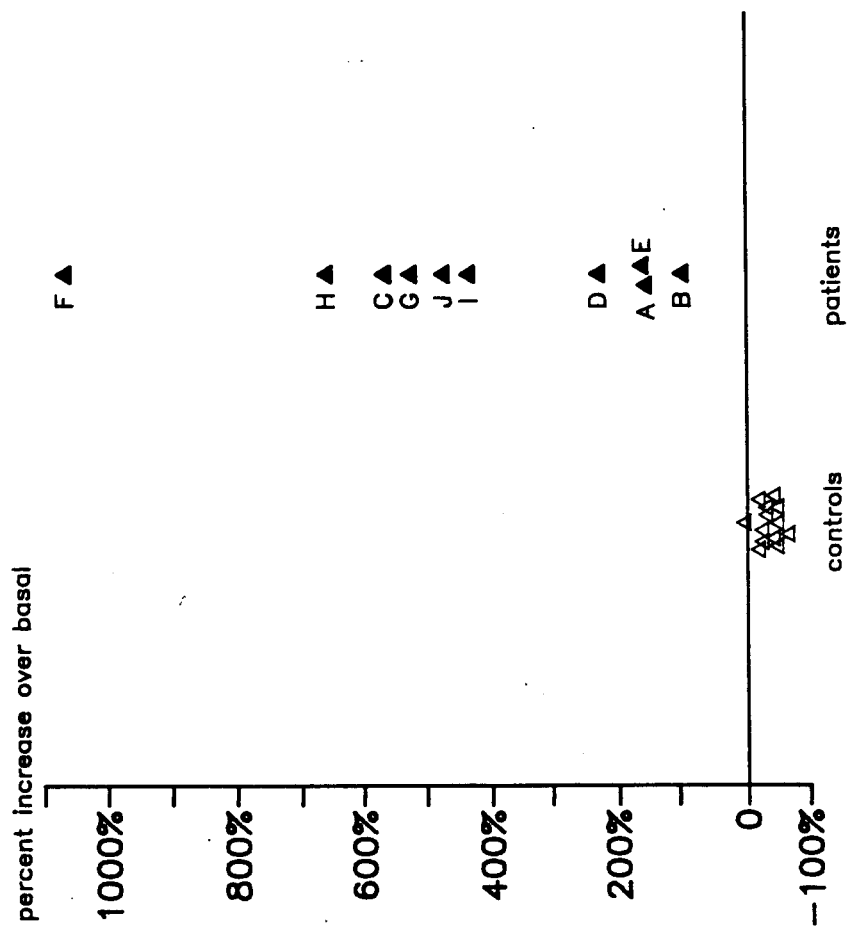
FIG. 5 is a graph depicting thyroid stimulating immunoglobulin (TSI) levels of ten patients with Graves' disease and control subjects. TSI activity is expressed as percentage increase of cAMP concentrations over basal levels.

TSI Serum Samples:

Ten patients (8 women and 2 men) with Graves' disease and high levels of TSI were identified after evaluation by FRTL-5 cell bioassay in the clinical chemistry laboratory. (FRTL-5 bioassay described below employing known TSH receptor recognition of various species hormones) Consecutive samples that had indices greater than 15 and sufficient serum remaining for further evaluation were chosen. Seven of the 10 had serum thyroxine values above the normal range and 9 of 10 had TSH levels below the euthyroid range by sensitive immunoradiometric assay [Boots-Celltech Sucrosep, Berkshire, UK, conducted as described in Klee and Hay, *J. Clin. Endocrinol. Metab.*, 64:461 (1987)]. (FIG. 5). For comparison serum from 13 normal subjects was examined for TSI at the same serum dilution as the patient sera. (FIG. 5).

TSI Bioassay:

FRTL-5 cells were maintained in Ham's F-12 medium supplemented with 5% calf serum and a 6-hormone preparation (6H) as described by Ambesi-Impiombato, supra. The cells were removed from flasks enzymatically, plated at 150,000 cells per well in 24 well plates, and grown in 6H medium for 4 days. The medium was then replaced with fresh medium supplemented with insulin only (1H) for 7 days prior to assay. The bioassay was a modification of that described by Kasagi et al., supra. Briefly, immunoglobulins were precipitated from 2 ml of serum with 6 ml 20% polyethylene glycol 6000 (Baker, Phillipsburg, N.J.), centrifuged at 2800×g for 20 minutes, and then reconstituted in 2.4 ml buffer (NaCl-free Hanks balanced salt solution, NaCl-free HBSS), containing 1 mM iso-butyl-methylxanthine (IBMX, Sigma, St. Louis) and 1.5% BSA. After washing the cells with HBSS, 150 ul of buffer was added to the wells plus varying concentrations of synthetic α-subunit peptides followed immediately by 150 ul of the crude immunoglobulin extract. The plates were incubated for 2 hours at 37° C., 5% $CO_2$ after which 100 ul of medium was removed and diluted in 900 ul 50 mM sodium acetate buffer, pH 6.2. cAMP content was determined by radioimmunoassay using the procedures described in Wray and Glinos, supra and Steiner et al., supra. Basal cAMP levels were determined in the absence of immunoglobulin extract and synthetic peptides for each plate. Basal and maximum levels were determined in quadruplicate; peptide effects were measured in duplicate at each concentration.

Percent increase in cAMP levels over basal was calculated as below:

$$\% \text{ increase} = 100 \times \left[ \frac{\text{pmoles cAMP sample}}{\text{pmoles cAMP basal}} - 1 \right]$$

Percent inhibition of TSI activity by the synthetic α-subunit peptides was calculated as follows:

$$\% \text{ inhibition} = 100 \times \left[1 - \frac{\% \text{ increase with peptide}}{\% \text{ increase without peptide}}\right]$$

For comparison some samples were also examined after purification with ammonium sulfate precipitation and gel permeation chromatograph on Sephadex G-25. Inhibitory activity of the peptides was determined in a bioassay utilizing FRTL-5 cells similar to the above procedure but with a different assay buffer (200 mM sucrose, 10% HBSS, 0.4% BSA). cAMP release into the medium was measured by RIA after 2.5 hours incubation at 37° C. Results were expressed as above.

Statistical Analysis.

cAMP levels in the presence of synthetic peptides were compared to maximum levels using student's T test for paired samples. Mean percent inhibition between different peptides were compared with student's T test for independent samples. Correlations were determined by Pearson's R.

As described above (Tables 3 and 4), peptides α26-46 and α31-45 exhibited the most potent binding inhibition and inhibition of adenylate cyclase stimulation by TSH on thyroid membranes and FRTL-5 cells. These two peptides were chosen to determine their respective abilities to inhibit the bioactivity of Graves' immunoglobulin (TSI). As controls, two peptides (α81-92 and α61-75) of similar composition but distinct amino acid sequences were also analyzed. These two control peptides showed little or no ability to inhibit TSH mediated cAMP generation in the previous study.

FIG. 5 shows the maximum percent increase in cAMP levels over basal in the TSI bioassay of serum from the 10 Graves' disease patients and the 13 controls. The values for the patients are lower in this assay than the original bioassay used for patient selection because of the dilution required for the study. The mean percent increase of the patient samples was 437±88%. The immunoglobulins from the normal subjects caused slight reduction in cAMP levels from basal results (−36.9±4.9%). This phenomenon was also noted in a previous study utilizing a similar bioassay technique (Kasagi, supra).

Figure 6:
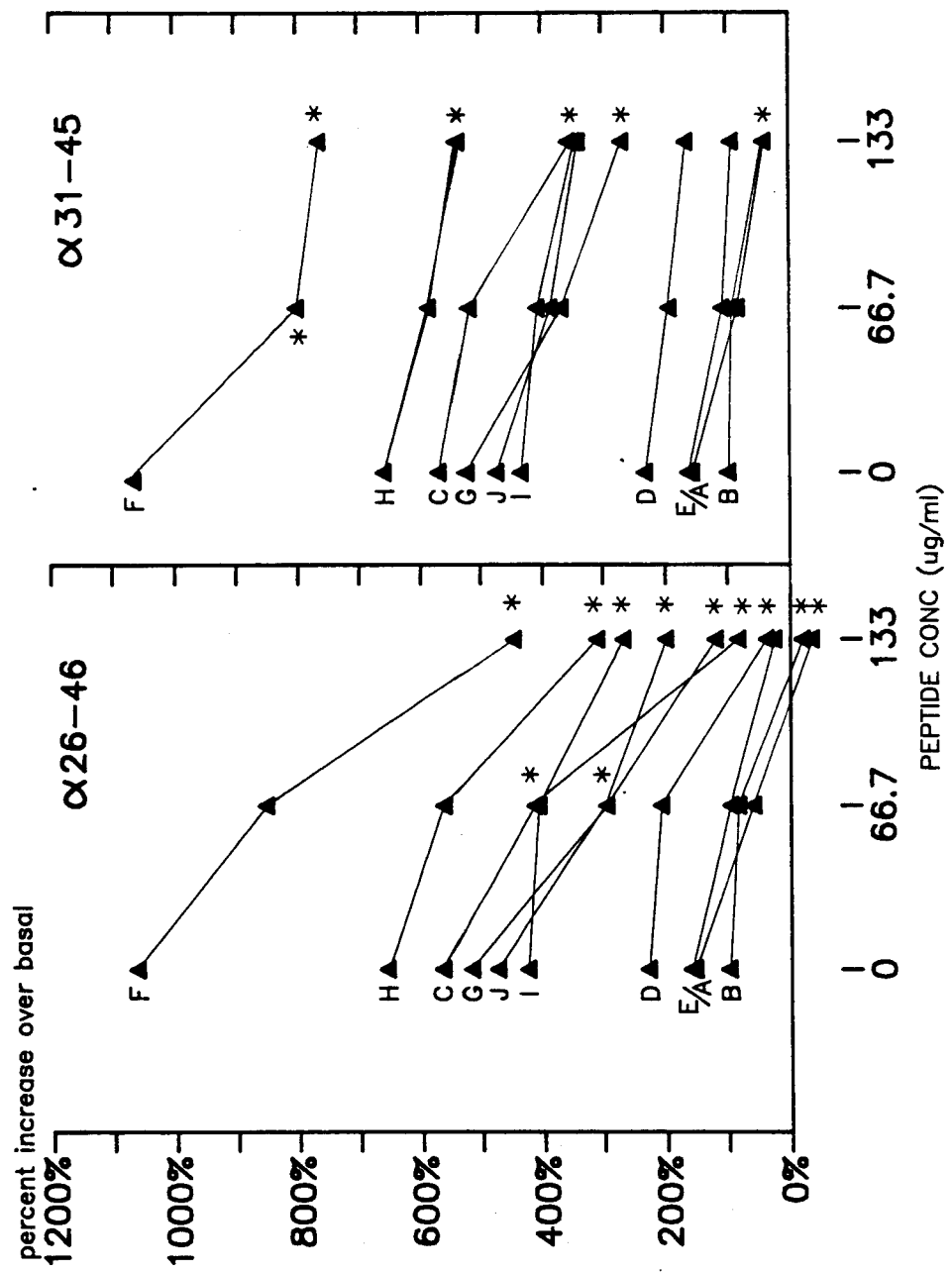
FIG. 6 is a graph depicting inhibition of thyroid stimulating immunoglobulin by active synthetic peptides.

The inhibitory effect of synthetic peptides α26-46 and α31-45 on cAMP generation in FRTL-5 cells stimulated by the 10 Graves' immunoglobulin preparations is demonstrated in FIG. 6 and table 5. As in the TSH binding and bioassays peptide α26-46 possessed surprisingly higher potency than α31-45, demonstrating 79.1±8.8% inhibition at 133 ug/ml versus 36.3±5.2% for α31-45 (p<0.001). At this concentration, α26-46 caused a significant (p<0.01) inhibitory effect in all 10 of the IgG samples assayed. Peptide α31-45 also lowered cAMP levels in all of the 9 samples tested at the same peptide concentration (133 ug/ml). This inhibition achieved statistical significance in six samples. It is believed that if more replicants had been performed, statistical significance would have been achieved in all 9; however, limitations in the amount of serum available prevented this.

Inhibition by α26-46 at the higher concentration ranged from 38±9.7% for serum I to 125.3±3% for serum A. Inhibition of cAMP to levels below basal also occurred with IgG from serum B. This phenomenon is a manifestation of the calculations, as the IgG of the normal patients reduced, slightly, the cAMP levels from basal (i.e. % increase = −36.9±4.9%). Thus, inhibition by peptide α26-46 to levels below basal in these two IgG samples represents complete inhibition of cAMP to the levels seen by normal immunoglobulins.

A significant negative correlation (r=0.65, p=0.01) was found between the maximum TSI activity and the percent inhibition achieved by peptide α26-46. (See FIG. 8) Thus, the more potent Ig samples were inhibited less completely by the peptide. However, with both α26-46 and α31-45 a dose response was seen, with higher levels of inhibition being achieved with larger doses of synthetic peptide (FIG. 6). As seen in FIG. 6, the slope of the dose response varied considerably among the 10 samples with both peptides.

TABLE 5

Percent inhibition of TSI activity from patient sera by synthetic peptides α26-46 and α31-45.

| | α26-46 | | α31-45 | |
|---|---|---|---|---|
| | concentration (ug/ml) | | | |
| Pt. sample | 66.7 | 133 | 66.7 | 133 |
| A | 62.1% | 125.3% | 45.0% | 71.7% |
| B | 14.3% | 125.0% | 13.1% | — |
| C | 29.1% | 86.4% | 8.6% | 37.4% |
| D | 9.1% | 85.7% | 16.6% | 28.9% |
| E | 42.0% | 85.9% | 34.6% | 43.1% |
| F | 19.8% | 57.8% | 24.8% | 28.0% |
| G | 43.1% | 77.2% | 29.7% | 49.6% |
| H | 14.7% | 52.5% | 11.1% | 19.2% |
| I | 4.2% | 38.0% | 6.9% | 20.3% |
| J | 36.0% | 57.7% | 18.7% | 28.7% |
| mean | 27.5% | 79.1% | 20.9% | 36.3% |
| s.e. | 5.5% | 8.8% | 3.7% | 5.2% |

For comparison, patient samples A–C were examined after ammonium sulfate precipitation and Sephadex G-25 chromatography. A different assay buffer was utilized (200 mM sucrose, 10% HBSS, 0.4% BSA) with the FRTL-5 cells and synthetic peptide α31-45. The peptide inhibited TSI activity in this assay by an amount equivalent to that seen with the previous assay (A, 73±5.2%; B, 65±6.2%; C, 77.4±0.5%). It is believed that these findings show that the inhibition by the peptides is not related to the TSI extraction procedure or the conditions utilized in the above described bioassay.

Figure 7:
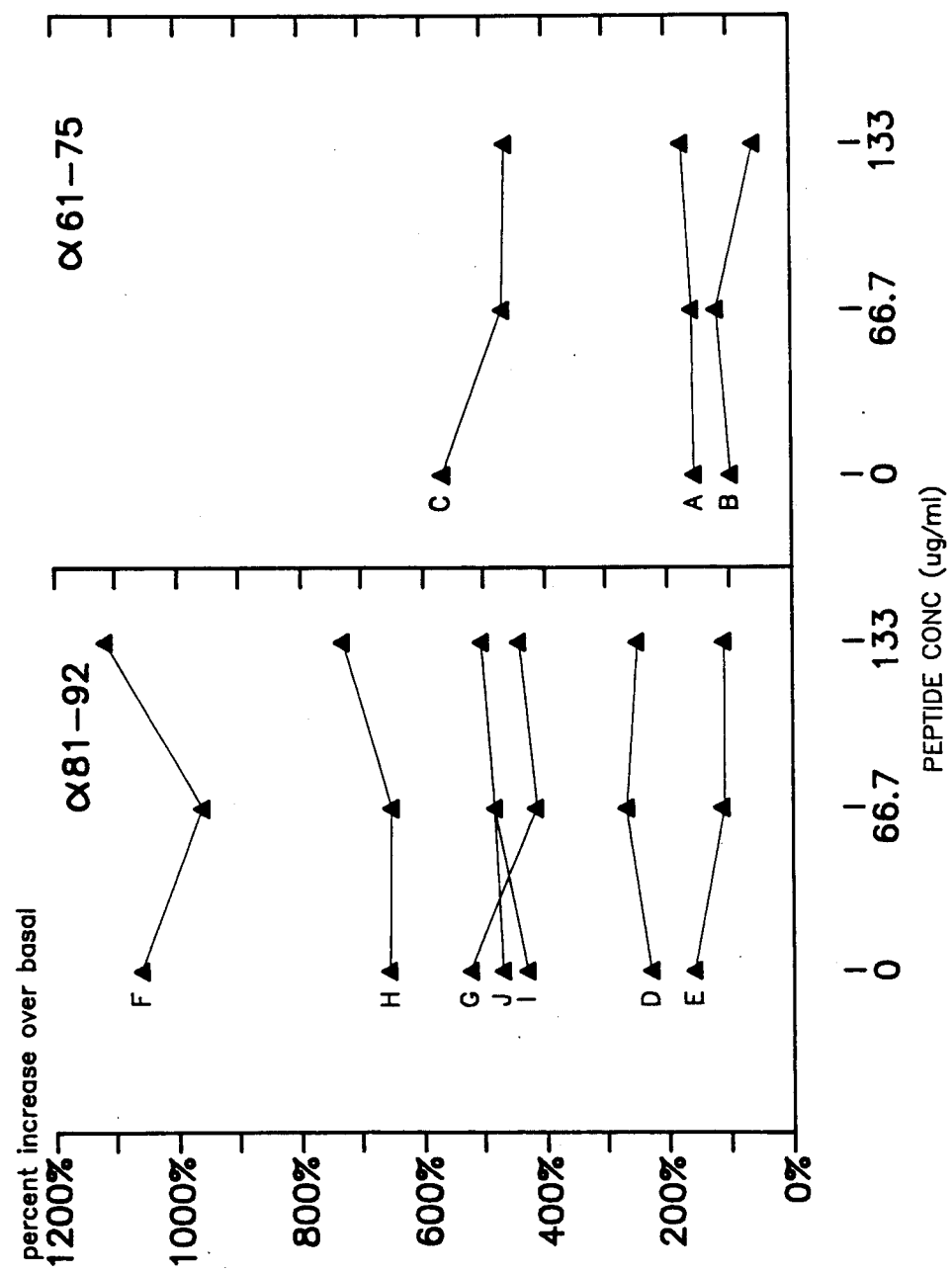
FIG. 7 is a graph depicting inhibition of thyroid stimulating immunoglobulin by control synthetic peptides.

As seen in FIG. 7 and Table 6, the control peptides α61-75 and α81-92 did not significantly inhibit the cAMP generated by patient immunoglobulin. At 133 ug/ml percent inhibition by α61-75 was 17.5±14% and was −0.1±6.2% by peptide α81-92. Furthermore, in none of the 3 Ig samples tested with α61-75 (patients A–C) and none of the 7 samples tested with α81-92 (patients D–J) were the cAMP levels in the presence of peptide statistically different from those found in the absence of the peptides.

TABLE 6

Percent inhibition of TSI activity from patient sera by control synthetic peptides α81-92 and α61-75.

| | α81-92 | | α61-75 | |
|---|---|---|---|---|
| | concentration (ug/ml) | | | |
| Pt. sample | 66.7 | 133 | 66.7 | 133 |
| A | | | −3.3% | −13.0% |
| B | | | −22.6% | 46.4% |
| C | | | 17.9% | 19.1% |
| D | −18.5% | −7.8% | | |
| E | 29.7% | 33.6% | | |
| F | 9.6% | −5.1% | | |
| G | 19.0% | 14.5% | | |

TABLE 6-continued

Percent inhibition of TSI activity from patient sera by control synthetic peptides α81-92 and α61-75.

| | α81-92 | | α61-75 | |
|---|---|---|---|---|
| | concentration (ug/ml) | | | |
| Pt. sample | 66.7 | 133 | 66.7 | 133 |
| H | 0.6% | −11.4% | | |
| I | −13.3% | −17.0% | | |
| J | −2.0% | −7.7% | | |
| mean | 3.6% | −0.1% | −2.7% | 17.5% |
| s.e. | 6.0% | 6.2% | 9.6% | 14.0% |

The synthetic peptides corresponding to α26-46 and α31-45 of the human glycoprotein hormones (TSH, LH, FSH, and hCG) have the ability to inhibit the cAMP stimulating effect of immunoglobulins from patients with Graves' disease in a bioassay designed to detect such immunoglobulins and possess the most potent inhibitory activity for TSH in both the radioreceptor and bioassay systems. Synthetic peptide α26-46 produced significant inhibition of TSI activity from all 10 patients in the bioassay system (FIG. 6). While FRTL-5 cells are not human thyroid tissue, as seen herein, we have not found significant interspecies differences in the binding activity of these same α-subunit peptides between FRTL-5 cells and human thyroid membranes. Also, the TSH receptor of these cells has been found to be structurally similar to that of other species including the human TSH receptor. [Furmaniak et al., *Acta Endo (Copenh)*, 115 (suppl. 281:157 (1987); Furmaniak et al., *Program of the 62nd Meeting of the American Thyroid Assoc.*, p. T-62 (1987)] Thus, we believe it is unlikely that the inhibition seen in this study is specific only for the FRTL-5 cell bioassay.

Figure 8:
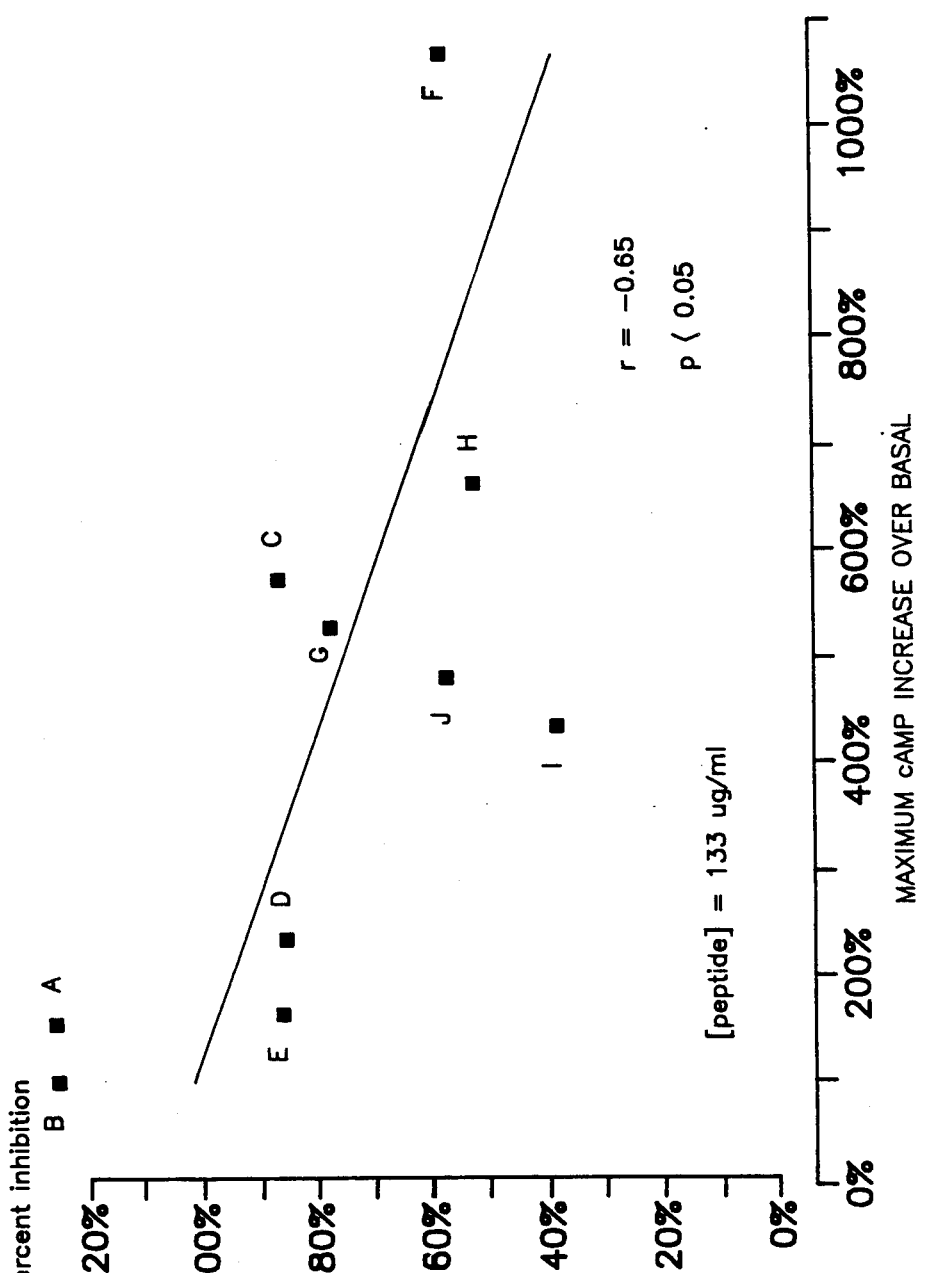
FIG. 8 is a graph depicting correlation of percent inhibition activity of the synthetic peptide corresponding to α-subunit region α26-46 and the maximum stimulating activity of thyroid stimulating immunoglobulin positive sera.

As noted above, we found a significant negative correlation between the maximum TSI activity and the percent inhibition achieved by the highest dose of peptide α26-46 tested (FIG. 8). As also noted, a dose response was seen in all of the 10 patient samples tested. We believe that these findings are due to differences in the titer and/or affinity of the TSI between individual patients. Thus, we believe it is likely that further inhibition can be achieved by increasing further the dose of the peptides.

As shown herein, the FRTL-5 cell line can be used successfully as a bioassay system for TSH with sensitivity ranging form 1 to 10 uU/ml TSH. The extraction procedure for the Graves' Ig used herein, however, removes the majority of TSH so that stimulation of adenylate cyclase does not occur until circulating levels of TSH are quite elevated (greater than 30 uU/ml, See Kasagi, supra). All of the serum samples tested herein had TSH levels well below these amounts and as expected the majority of the Graves' patients had undetectable TSH levels by a sensitive immunoradiometric assay. It is not possible therefore, that the inhibitory effect of the synthetic peptides was due to a reduction of TSH stimulation rather than the inhibition of Graves' Ig activity.

In accordance with the present invention, the data herein indicates that synthetic peptides corresponding to regions of the α-subunit of human glycoprotein hormones, including the synthetic peptide corresponding to amino acids α31-45, and most preferably the synthetic peptide corresponding to amino acids α26-46 have broad utility. These peptides exhibit important biological activity including inhibition of TSH binding to human thyroid membrane and rat FRTL-5 cells; inhibition of TSH stimulation of cAMP production; and inhibition of the stimulatory effect of TSI from patients with Graves' disease in an in vitro bioassay. Therefore, it is believed these synthetic peptides can be useful as therapeutic or diagnostic agents.

It is further recognized that the practical usefulness of the peptides derived from regions of the α-subunit (such as 26-46 and 31-45) can be enhanced by modifications that would (1) inhibit proteolytic cleavages and thus prolong their circulatory half-life, (2) increase immunogenicity and/or (3) increase intrinsic biological activity. Therefore, peptides of the present invention, envision synthetic peptides corresponding to specific α-subunit such as 26-46 and 31-45 and analogous peptides that have been modified by any of the following:

(1) deletion of amino acids at particular locations in the sequence(s);

(2) substitution of residues in the sequence(s) with any of the 20 common L-amino acids or their natural metabolic derivatives (i.e. hydroxyproline, hydroxylysine, etc.) or their D-amino acid counterparts, either L or D forms of amino acids that occur naturally but are not found in proteins or peptides (ornithine and citrulline for example) or synthetic amino acids of either L or D form such as norleucine and norvaline;

(3) chemical modifications which sulfonate, phosphorylate, halogenate, nitrate, nitrosylate or oxidize susceptible residues in the sequence;

(4) chemical modifications which acylate or alkylate susceptible residues including the N-terminus (such modifying agents might include adjuvants such as N-acetylmuramic acid);

(5) chemical modifications which leave the Cterminus as a free carboxyl group and esterifications of this free carboxyl group; and (6) any chemical modification of susceptible residues such as the N-terminus, the C-terminus, cysteine, methionine, tyrosine, arginine, lysine, serine and threonine.

What is claimed is:

1. A polypeptide corresponding substantially to an α-subunit region of human glycolprotein hormones having specific binding capacity for human thyroid membrane and FRTL-5 rat thyroid cell receptors; said polypeptide exhibiting the ability to inhibit TSH mediated cAMP generation by human thyroid membrane and FRTL-5 rat thyroid cells and the ability to inhibit stimulatory ability of thyroid stimulating immunoglobulin, and corresponding to an amino acid sequence from within an overall amino acid sequence from about amino acid α21 to about amino acid α46 of said human glycoprotein hormone and having at least about 15 amino acid residues in the sequence.

2. The polypeptide of claim 1 wherein said polypeptide inhibits TSH mediated cAMP generation by between about 90 and 100%.

3. A polypeptide of the formula:

Leu-Gln-Cys-Met-Gly-Cys-Cys-Phe-Ser-Arg-Ala-Tyr-Pro-Thr-Pro-Leu-Arg-Ser-Lys-Lys-Thr ($NH_2$).

4. A polypeptide of the formula:

Pro-Gly-Ala-Pro-Ile-Leu-Gln-Cys-Met-Gly-Cys-Phe-Ser-Arg.

5. A polypeptide of the formula:

Cys-Cys-Phe-Ser-Arg-Ala-Tyr-Pro-Thr-Pro-Leu-Arg-Ser-Lys-Lys.

6. A method for inhibiting stimulatory ability of thyroid stimulating immunoglobulin comprising the step of: treating human cells in vitro, that bind thyroid stimulating immunoglobulin with a synthetic polypeptide selected from the group of polypeptide sequences consisting essentially of polypeptides corresponding to human glycoprotein hormone α-subunit amino acid regions α31-45 and α26-46.

7. The method of claim 6 wherein said polypeptide is:

Leu
Gln-Cys-Met-Gly-Cys-Phe-Ser-ARg-Ala-Tyr-
Pro-Thr-Pro-Leu-Arg-Ser-Lys-Lys-Thr(NH$_2$).

* * * * *

UNITED STATES PATENT AND TRADEMARK OFFICE
CERTIFICATE OF CORRECTION

PATENT NO. : 4,973,578

DATED : November 27, 1990

INVENTOR(S) : Robert J. Ryan et al.

Page 1 of 2

It is certified that error appears in the above-identified patent and that said Letters Patent is hereby corrected as shown below:

On the Title page, Item [54] and Col. 1, line 3, "LYCOPROTEIN" should read --GLYCOPROTEIN--.

At column 4, line 50 after "peptides" insert --.--.

At column 6, line 9 after "(0.5 M" insert --solution in--.

At column 6, line 9 for "(w/w));" read --(w/v));--.

At column 6, line 10 for "dicyclohexylorea" read --dicyclohexylurea--.

At column 6, line 14 for "DPIF" read --DMF--.

At column 6, line 17 for "(2ed 1984)" read --(2d ed. 1984)--.

At column 7, line 52 for "o-Subunit" read --$\alpha$-Subunit--.

At column 9, line 19 for "52.5 X 6.6%" read --52.5 $\pm$ 6.6%--.

At column 9, line 51 for "mean + s.e." read --mean $\pm$ s.e.--

At column 9, line 56 for "100.63 + 0.90" read --100.63 $\pm$ 0.90--.

At column 10, line 6 for "mean + s.e." read --mean $\pm$ s.e.--.

At column 14, lines 34-35 for "Cterminus" read --C-terminus--.

At column 14, in claim 4, line 2 after "Cys-" (2nd Occurrence) insert --Cys--.

At column 16, in claim 7, line 2 delete "Leu".

At column 16, in claim 7, line 3 before "Gln-" insert --Leu- --.

UNITED STATES PATENT AND TRADEMARK OFFICE
CERTIFICATE OF CORRECTION

PATENT NO. : 4,973,578

DATED : November 27, 1990

INVENTOR(S) : Robert J. Ryan et al.

It is certified that error appears in the above-identified patent and that said Letters Patent is hereby corrected as shown below:

At column 16, in claim 7, line 3 after "Cys-" (2nd) insert --Cys- --.

At column 16, in claim 7, line 3 for "ARg" read --Arg--.

Signed and Sealed this

Eighteenth Day of May, 1993

MICHAEL K. KIRK

*Acting Commissioner of Patents and Trademarks*